United States Patent
Bockow

(10) Patent No.: US 9,393,251 B2
(45) Date of Patent: Jul. 19, 2016

(54) COMPOSITIONS AND METHODS FOR TREATING SEVERE THROMBOCYTOPENIA RELATED DISEASE

(71) Applicant: Barry I. Bockow, Seattle, WA (US)

(72) Inventor: Barry I. Bockow, Seattle, WA (US)

(*) Notice: Subject to any disclaimer, the term of this patent is extended or adjusted under 35 U.S.C. 154(b) by 0 days.

(21) Appl. No.: 14/184,332

(22) Filed: Feb. 19, 2014

(65) Prior Publication Data

US 2014/0274976 A1  Sep. 18, 2014

Related U.S. Application Data

(60) Provisional application No. 61/785,360, filed on Mar. 14, 2013.

(51) Int. Cl.
*A01N 45/00* (2006.01)
*A61K 31/59* (2006.01)
*A61K 31/593* (2006.01)
*A61K 31/4706* (2006.01)
*A61K 31/573* (2006.01)

(52) U.S. Cl.
CPC ........... *A61K 31/593* (2013.01); *A61K 31/4706* (2013.01); *A61K 31/573* (2013.01)

(58) Field of Classification Search
None
See application file for complete search history.

(56) References Cited

PUBLICATIONS

Arnal et al., "Treatment of Severe Immune Thrombocytopenia Associated with Systemic Lupus Erythematosus: 59 Cases," The Journal of Rheumatology, 2002; 29:1.*
Schwalfenberg, "Solar Radiation and Vitamin D: Mitigating Environmental Factors in Autoimmune Disease," Journal of Environmental and Public Health, vol. 2012, Article ID 619381, 9 pages.*
Thota S., Kistangari G., Daw H., Spiro, T.: Immune thrombocytopenia in adults: an update. Clev Clin J Med 2012, 79(9):641-650.
Newman, G.C. et al.: A dose of 75mu g/kg/d i.v. anti-D increases the platelet count more rapidly and . . . , Br J Haematol 2001, 112(4):1076-1078.
Arnold, D.M., et al.: Systematic review: efficacy and safety of rituximab for adults with idiopathic thrombocytopenic purpura. Ann Intern Med 2007, 146(1):25-33.
Boruchov, D.M., et al.: Multiagent induction and maintenance of therapy for patients with refractory immune thrombocytopenic purpura (ITP). Blood 2007, 110(10):3526-3531.
Kojouri, K., et al.: Splenectomy for adult patients with idiopathic thrombocytopenic purpura: a systematic review . . . , Blood 2004, 104(9):2623-2634.
Portielje, J.E., et al.: Morbidity and mortality in adults with idiopathic thrombocytopenic purpura. Blood 2001, 97(9):2549-2554.
McMillan, R., et al.: Suppression of in vitro megakaryocyte production by antiplatelet autoantibodies from adult patients with chronic ITP. Blood 2004, 103(4):1364-1369.
Khan, M., Mikhael J.: A review of immune thrombocytopenic purpura: focus on the novel thrombopoietin agonists. J Blood Med 2010, 1:21-31.
Muller, K., et al.: Inhibition of production and function of interleukin-6 by 1,25-dihydroxyvitamin D3. Immunol Lett 1991, 28(2):115-120. [abstract: retrieved Jun. 16, 2014].
Veldman, C.M., et al.: Expression of 1,25-dihydroxyvitamin D(3) receptor in the immune system. Arch Biochem Biophys 2000, 374(2):334-338. [abstact: retrieved Jun. 17, 2014].
Andersson, J.: Cytokines in idiopathic thrombocytopenic purpura (ITP). Acta Paediatr Suppl 1998, 424:61-64. [abstract: retrieved Jun. 17, 2014].
Semple, J.W., Freedman, J.: Increased antiplatelet T helper lymphocyte reactivity in patients with autoimmune thrombocytopenia. Blood 1991, 78(10):2619-2625.
Cantorna, M.T., et al.: 1,25-Dihydroxyvitamin D3 reversibly blocks the progression of relapsing encephalomyelitis . . . , Proc Natl Acad Sci USA 1996, 93(15):7861-7864.
Pedersen, L.B., et al.: 1,25-Dihydroxyvitamin D3 reverses experimental autoimmune encephalomyelitis . . . , J Neurosci Res 2007, 85(11):2480-2490. [abstract: retrieved Jun. 16, 2014].
Cantorna, M.T., et al.: 1,25-Dihydroxyvitamin D3 is positive regulator for the two anti-encephalitogenic cytokines TGF-beta 1 and IL-4. J Immunol 1998, 160(11):5314-5319.
Shevach, E.M.: Regulatory/supressor T cells in health and disease. Arthritis Rheum 2004, 50(9):2721-2724.
Iran, D.Q., et al.: Induction of FOXP3 expression in naive human CD4 +FOXP3 T cells by T-cell receptor stimulation . . . , Blood 2007, 110(8):2983-2990.
Unger, W.W., et al.: Induction of Treg by monocyte-derived DC modulated by vitamin D3 or dexamethasone: differential role for PD-L1. Eur J Immunol 2009, 39(11):3147-3159.
Marmor, M.F., Carr, et al.: Recommendations on screening for chloroquine . . . , Ophthalmology 2002, 109(7):1377-1382. [p. 1377].
Nandakumar A., et al.: Myeloid leukaemia following therapy for a first primary cancer. Br J Cancer 1991, 63(5):782-788.
Kulie, Teresa, et al., Vitamin D: An Evidence-Based Review, Journal of the American Board of Family Medicine, vol. 22, No. 6, Nov.-Dec. 2009, pp. 698-706.

* cited by examiner

*Primary Examiner* — Jared D Barsky
(74) *Attorney, Agent, or Firm* — Betts, Patterson & Mines, P.S.

(57) ABSTRACT

Compositions and methods of treating severe thrombocytopenia and related disease are provided.

5 Claims, No Drawings

COMPOSITIONS AND METHODS FOR TREATING SEVERE THROMBOCYTOPENIA RELATED DISEASE

CROSS-REFERENCE TO RELATED APPLICATION

This application claims the benefit of U.S. Provisional Application No. 61/785,360 filed Mar. 14, 2013, incorporated by reference herein.

BACKGROUND

Immune thrombocytopenic purpura ("ITP") is an autoimmune disorder in which platelets are targeted by the host immune system. The incidence of ITP is approximately 2.5 per 100,000 persons per year. Platelet depletion occurs when autoantibodies targeting glycoproteins found on the surface of platelets opsonize the cells, resulting in destruction by macrophages. These antibodies can also bind to megakaryocytes and prevent complete maturation, which results in lowered levels of platelet production. The goal of treatment is to keep the platelet count above $3 \times 10^4/mm^3$ to prevent major internal organ bleeding.

Several treatments are currently in use in the clinical setting that increase platelet counts, including steroid and immunosuppressive therapy. Current treatment involves intravenous corticosteroids, immunosuppressants such as mycophenolatemofetil and azathioprine, Cytoxan® (cyclophosphamide), and intravenous immunoglobulin (IVIg). Anti-D immunoglobulin can only be given to RhD-positive individuals, thus limiting treatment options for RhD-negative persons. Rituximab, a chimeric monoclonal antibody, has also been tried as an experimental treatment, and combinations of therapies have been used with some success.

Each of these therapies may be associated with significant side effects and efficacy is often temporary, requiring either additional and/or alternative treatment. Many of the side effects of steroids are well known and include hypertension, diabetes, osteoporosis and adrenal insufficiency. Several of these drugs are carcinogenic and there have been reports of malignancy formation after treatment, for example a high risk of acute myelogenous leukemia after Cytoxan® treatment. Response rates vary, and there is currently no consensus regarding the appropriate treatment protocol for this condition. Corticosteroids show efficacy in 50% to 80% of cases, but if treatment is stopped, the remission rate is only 10% to 30%.

If patients are refractory to drug treatments, splenectomy is a second line option; two-thirds of patients who undergo splenectomy for ITP respond to the treatment. However, complications may arise from this surgical procedure including hemorrhage, abscess, sepsis, thrombosis and death and relapse of ITP occurs in a median of 15% of patients. These patients are at lifelong risk for infection from *Streptococcus pneumoniae, Neisseria meningitides* and *Haemophilus influenza.*

Due to the side effects of current treatments for ITP, caution must be used, and aggressive treatment should be reserved for patients with severe and symptomatic thrombocytopenia. In addition to side effects and limited efficacy, current treatments involving anti-cancer or biologics can be very expensive. Intravenous infusions of biologics and immunoglobulin can be $10,000 or more per infusion. Current treatments also may involve hospitalization, and in some cases care in the intensive care unit. Such high costs are also burdensome to society and governments, who often absorb the costs directly and indirectly. The need therefore exists for alternative treatments for ITP and other autoimmune disease that have less side effects and are cost effective. The present disclosure addresses this and other needs. Applicants have found a treatment for ITP and other autoimmune diseases that is safe and effective and costs as little as $100 or less per month, which is extremely inexpensive compared to current treatments.

SUMMARY OF THE INVENTION

This summary is provided to introduce a selection of concepts that are further described below in the Detailed Description.

In one aspect, the present disclosure provides pharmaceutical compositions for the treatment of immune thrombocytopenic purpura and other autoimmune diseases. In some embodiments, the compositions comprise Vitamin D and hydroxychloroquine. In some embodiments, the compositions comprise Vitamin D, hydroxychloroquine, and a corticosteroid.

In one aspect, the present disclosure provides methods of treating immune thrombocytopenic purpura and other autoimmune diseases. In some embodiments, the methods comprise administering to a subject in need thereof a composition comprising vitamin D and hydroxychloroquine. In some embodiments, the methods comprise administering to a subject in need thereof a composition comprising Vitamin D, hydroxychloroquine, and a corticosteroid.

DETAILED DESCRIPTION

Unless specifically defined herein, all terms used herein have the same meaning as they would to one skilled in the art of the present disclosure.

In one aspect, the present disclosure provides pharmaceutical compositions for the treatment of immune thrombocytopenic purpura and other autoimmune diseases. In some embodiments, the compositions comprise Vitamin D and hydroxychloroquine. In some embodiments, the compositions comprise Vitamin D, hydroxychloroquine, and a corticosteroid.

As used herein, the term "Vitamin D" refers to 1a,25-dihydroxy cholecalciferol or 1a,25-dihydroxy vitamin $D_3$. Vitamin D suitable for use in the compositions of the present disclosure may be either natural or artificially synthesized. In addition to the active ingredients of Vitamin D, hydroxychloroquine, and, in some embodiments, corticosteroid, the compositions may contain pharmaceutically acceptable inactive excipients. Excipients may include, but are not limited to, diluents, binders, fillers, disintegrants, lubricants, coatings, and preservatives.

In some embodiments, the compositions comprise Vitamin D in a concentration of from about 2,000 IU (International Units) to about 15,000 IU per unit dosage form, or any amount in the range of between about 2,000 IU and about 15,000 IU. In some embodiments, the compositions comprise Vitamin D in a concentration of about 3,500 IU per unit dosage form. In some embodiments, the compositions comprise Vitamin D in a concentration of about 7,500 IU per unit dosage form.

In some embodiments, the compositions comprise hydroxychloroquine in a concentration of from about 200 mg to about 400 mg per unit dosage form, or any amount in the range of between about 200 mg and 400 mg. In some embodiments, the compositions comprise hydroxychloroquine in a concentration of about 200 mg per unit dosage form. In some embodiments, the compositions comprise hydroxychloroquine in a concentration of about 400 mg per unit dosage form.

In one embodiment, a pharmaceutical composition of the present disclosure comprises Vitamin D in a concentration of about 3500 IU per unit dosage form and hydroxychloroquine in a concentration of about 200 mg per unit dosage form. In one embodiment, a pharmaceutical composition of the present disclosure comprises Vitamin D in a concentration of about 7500 IU per unit dosage form and hydroxychloroquine in a concentration of about 200 mg per unit dosage form. In one embodiment, a pharmaceutical composition of the present disclosure comprises Vitamin D in a concentration of about 15,000 IU per unit dosage form and hydroxychloroquine in a concentration of about 400 mg per unit dosage form.

In some embodiments the compositions further comprise a corticosteroid. Prednisone is an example of a suitable corticosteroid for use in the pharmaceutical compositions of the present disclosure. Other corticosteroids, including, but not limited to, cortisone and hydrocortisone are also suitable. In some embodiments, the compositions further comprise a corticosteroid in a concentration from about 1 mg per unit dosage form to about 20 mg per unit dosage form, or any amount in the range between about 1 mg per unit dosage form and about 20 mg per unit dosage form. In some embodiments, the compositions further comprise a corticosteroid in a concentration from about 2 mg per unit dosage form to about 15 mg per unit dosage form.

In one embodiment, a pharmaceutical composition of the present disclosure comprises Vitamin D in a concentration of about 3500 IU per unit dosage form, hydroxychloroquine in a concentration of about 200 mg per unit dosage form, and a corticosteroid in a concentration of about 2.5 mg per unit dosage form. In one embodiment, a pharmaceutical composition of the present disclosure comprises Vitamin D in a concentration of about 7500 IU per unit dosage form, hydroxychloroquine in a concentration of about 200 mg per unit dosage form, and a corticosteroid in a concentration of about 7.5 mg per unit dosage form. In one embodiment, a pharmaceutical composition of the present disclosure comprises Vitamin D in a concentration of about 15,0000 IU per unit dosage form, hydroxychloroquine in a concentration of about 400 mg per unit dosage form, and a corticosteroid in a concentration of about 15 mg per unit dosage form.

In some embodiments, the compositions of the present disclosure may be used to treat other blood disorders such as immune-related leucopenia, and bone marrow failure, and autoimmune diseases such as systemic lupus erythematosus, rheumatoid arthritis, scleroderma, and Sjögren's syndrome.

In one aspect, the present disclosure provides methods for the treatment of immune thrombocytopenic purpura and other autoimmune diseases. In some embodiments, the methods comprise administering a pharmaceutical composition comprising Vitamin D and hydroxychloroquine to a patient in need thereof. In some embodiments, the methods comprise administering a pharmaceutical composition comprising Vitamin D, hydroxychloroquine, and a corticosteroid to a patient in need thereof.

In some embodiments, the methods of the present disclosure for the treatment of immune thrombocytopenic purpura comprise the steps of: (a) administering to a patient twice a day a unit dosage form of a pharmaceutical composition comprising Vitamin D in a concentration of about 7500 IU per unit dosage form and hydroxychloroquine in a concentration of about 200 mg per unit dosage form; and (b) repeating step (a) daily for a period of time until the patient's serum Vitamin D concentration reaches the amount of about 40 ng/mL to about 50 ng/mL and the patient's platelet count reaches or exceeds the amount of 140,000 mm$^3$.

In some embodiments, the methods further comprise a step (c) of administering to a patient twice a day a unit dosage form of a pharmaceutical composition comprising Vitamin D in a concentration of about 3500 IU per unit dosage form and hydroxychloroquine in a concentration of about 200 mg per unit dosage form for a period of time to maintain the patient's serum Vitamin D concentration at the amount of about 40 ng/mL to about 50 ng/mL and the patient's platelet count at or greater than the amount of 140,000 mm$^3$. The maintenance dosage can be continued for a period of months and years.

Although methods have been described that comprise administering unit dosage forms of a composition comprising Vitamin D and hydroxychloroquine twice a day, it is to be understood that methods comprising administering the equivalent daily dose once a day (e.g. 15,000 IU Vitamin D and 400 mg hydroxychloroquine), or more than twice a day, are also included within the scope of the present disclosure.

In some embodiments, the methods of the present disclosure for the treatment of immune thrombocytopenic purpura comprise the steps of: (a) administering to a patient twice a day a unit dosage form of a pharmaceutical composition comprising Vitamin D in a concentration of about 7500 IU per unit dosage form, hydroxychloroquine in a concentration of about 200 mg per unit dosage form, and a corticosteroid in a concentration of about 7.5 mg per unit dosage form; and (b) repeating step (a) daily for a period of time until the patient's serum Vitamin D concentration reaches the amount of about 40 ng/mL to about 50 ng/mL and the patient's platelet count reaches or exceeds the amount of 140,000 mm$^3$.

In some embodiments, the methods further comprise a step (c) of administering to a patient twice a day a unit dosage form of a pharmaceutical composition comprising Vitamin D in a concentration of about 3500 IU per unit dosage form, hydroxychloroquine in a concentration of about 200 mg per unit dosage form, and a corticosteroid in a concentration of about 1 mg per unit dosage form for a period of time to maintain the patient's serum Vitamin D concentration at the amount of about 40 ng/mL to about 50 ng/mL and the patient's platelet count at or greater than the amount of 140,000 mm$^3$.

In some embodiments, the methods further comprise a step (c) of administering to a patient twice a day a unit dosage form of a pharmaceutical composition comprising Vitamin D in a concentration of about 3500 IU per unit dosage form and hydroxychloroquine in a concentration of about 200 mg per unit dosage form for a period of time to maintain the patient's serum Vitamin D concentration at the amount of about 40 ng/mL to about 50 ng/mL and the patient's platelet count at or greater than the amount of 140,000 mm$^3$. The maintenance dosage can be continued for a period of months or years.

In some embodiments, the methods of the present disclosure for the treatment of immune thrombocytopenic purpura comprise the steps of: (a) administering to a patient a unit dosage form of a pharmaceutical composition comprising Vitamin D in a concentration of about 7500 IU per unit dosage form and hydroxychloroquine in a concentration of about 200 mg per unit dosage form; (b) administering to the patient a corticosteroid in a concentration of about 2 mg to about 20 mg per unit dosage form; (c) repeating steps (a) and (b) twice a day; and (d) repeating step (c) daily for a period of time until the patient's serum Vitamin D concentration reaches the amount of about 40 ng/mL to about 50 ng/mL and the patient's platelet count reaches or exceeds the amount of 140,000 mm$^3$.

In some embodiments, the methods further comprise a step (e) of administering to a patient twice a day a unit dosage form of a pharmaceutical composition comprising Vitamin D in a concentration of about 3500 IU per unit dosage form and hydroxychloroquine in a concentration of about 200 mg per unit dosage form for a period of time to maintain the patient's serum Vitamin D concentration at the amount of about 40 ng/mL to about 50 ng/mL and the patient's platelet count at or greater than the amount of 140,000 mm$^3$. The maintenance dosage can be continued for a period of months or years.

Although exemplary treatment regimens have been described, it is to be understood that the scope of the present disclosure includes daily dosages that are varied according to the needs of the patient.

In some embodiments, the methods of the present disclosure may be used to treat other blood disorders such as immune-related leucopenia, and bone marrow failure, and autoimmune diseases such as systemic lupus erythematosus, rheumatoid arthritis, scleroderma, and Sjögren's syndrome. In those embodiments, the methods comprise administering to a patient in need thereof compositions of the present disclosure in amounts comparable to the amounts used to treat immune thrombocytopenic purpura and over a period of time needed to relieve the patient's symptoms and to maintain an improved state of relief.

In some embodiments, the methods of the present disclosure may be used to change or modify a population of T-cells in a subject comprising administering a pharmaceutical composition comprising Vitamin D and hydroxychloroquine to a patient in need thereof.

The foregoing may be better understood in connection with the following representative examples, which are presented for purposes of illustration and not by way of limitation.

EXAMPLES

The following examples report cases of patients with severe immune thrombocytopenic purpura who failed conventional therapies and who responded to treatment of high-doses of Vitamin D (50,000 IU to 150,000 IU per week) and hydroxychloroquine (Plaquenil®).

Example 1

A 79-year-old Caucasian man was referred for management of severe ITP. Serology was positive for both anti-SSA/Ro autoantibodies ("SSA") and antinuclear antibodies ("ANA") suggesting that the patient had an overlap of systemic lupus erythematosus ("SLE") and/or Sjögren's syndrome. In addition, he was cytopenic and complained of dry eyes and mouth (sicca symptoms) and joint pain, which are secondary symptoms of SLE and/or Sjögren's syndrome. He also had a borderline low 25-hydroxy (25-OH) vitamin D level of 34 ng/mL. No evidence of an underlying malignancy responsible for this life-threatening hematologic condition was found. The patient received WinRho® (IV Immune globulin, or IVIg) and high-dose corticosteroid (prednisone—60 mg/day) after his platelet count had dropped to 9000/mm$^3$ (normal>140,000/mm$^3$). The platelet count only increased to 43,000/mm$^3$ after the immunoglobulin/steroid treatment.

As indicated in Table 1 below, the patient was administered the following treatments over a period of time:

TABLE 1

| Initial Platelet Count Before Treatment: 43,000/mm$^3$ | | | | | |
|---|---|---|---|---|---|
| Treatment | A | B | C | D | E |
| Plaquenil ® | 200 mg Twice/day | 200 mg Twice/day | 200 mg Twice/day | 200 mg Twice/day | 200 mg Twice/day |
| Prednisone | 15 mg Once/day | 10 mg Once/day | 5 mg Once/day | 5 mg Once/day | 5 mg Once/day |
| Vitamin D | 50,000 IU Once/week | 150,000 IU Once/week | 50,000 IU Twice/week | 50,000 IU Twice/week | 0-IU |
| Time Period | 2 weeks | ~10 weeks | 1 month | 6 months | 1 month |
| Platelet Count | 55,000/mm$^3$ | 114,000/mm$^3$ | 141,000/mm$^3$ | 140,000/mm$^3$ | 18,000/mm$^3$ |
| Treatment | F | G | H | I | |
| Plaquenil ® | 200 mg Twice/day | 200 mg Twice/day | 200 mg Twice/day | 200 mg Twice/day | |
| Prednisone | 30 mg Once/day | 30 mg Once/day | 5 mg Once/day | 0 mg Once/day | |
| Vitamin D | 50,000 IU Twice/week | 50,000 IU Twice/week | 50,000 IU Twice/week | 50,000 IU Once/week | |
| Time Period | 3 weeks | 1 month | 4 months | 6 weeks | |
| Platelet Count | 91,000/mm$^3$ | 137,000/mm$^3$ | 161,000/mm$^3$ | 215,000/mm$^3$ | |

The patient's platelet count was 215,000/mm$^3$ six weeks after discontinuing prednisone, indicating a regimen of hydroxychloroquine at a dose of 200 mg twice a day and Vitamin D at a dose of 50,000 IU once a week was sufficient to maintain a stable count. The patient remained stable without the administration of prednisone. Furthermore, even with high-dose of Vitamin D, there were no significant changes in calcium, phosphate, or creatinine levels.

Results.

The data in Table 1 illustrate that a combination of hydroxychloroquine and high doses of Vitamin D produced a dramatic increase in the patient's platelet count. Prior immunoglobulin infusions and high doses of prednisone had only increased the patient's platelet count from 9,000 mm$^3$ to 43,000 mm$^3$, which is still extremely low. However, the combination treatment of Vitamin D and hydroxychloroquine was successful in raising the patient's platelet count over time from 43,000 mm$^3$ to 215,000 mm$^3$. Furthermore, as can be seen from the above treatment regimen, hydroxychloroquine at a dose of 200 mg twice a day and Vitamin D at a dose of 50,000 IU once a week was sufficient to maintain a stable platelet count.

These results are in sharp contrast to the results obtained with a combination of hydroxychloroquine and prednisone, without Vitamin D, which resulted in a dramatic decrease in platelet count, from 140,000 mm³ to 18,000 mm³ (see Treatment E). The platelet count was restored over time with the resumption of Vitamin D in the treatment regimen (see Treatment F-I). These results indicate that Vitamin D and hydroxychloroquine act in a synergistic manner to achieve and maintain a platelet count at or above normal levels.

Example 2

An 87-year-old Caucasian woman was referred with a platelet count of 8000/mm³. She presented with an ANA at 1:640, positive SSA, complained of dry eyes and dry mouth, and was cytopenic. Her total complement was also elevated at 86 hemolytic units. The patient was felt to have an overlap syndrome of SLE and Sjögren's with an immune thrombocytopenia. Her initial 25-hydroxy (25-OH) vitamin D level was 17 ng/mL.

As indicated in Table 2 below, the patient was administered the following treatments over a period of time:

TABLE 2

| Initial Platelet Count Before Treatment: 8,000/mm³ | | | | | |
|---|---|---|---|---|---|
| Treatment | A | B | C | D | E |
| Plaquenil ® | 200 mg Twice/day | 200 mg Twice/day | 200 mg Twice/day | 200 mg Twice/day | 200 mg Twice/day |
| Prednisone | 40 mg Once/day | 15 mg Once/day | 7.5 mg Once/day | 7.5 mg Once/day | 5 mg Once/day |
| Vitamin D | 50,000 IU Once/week | 50,000 IU Once/week | 50,000 IU Once/week | 50,000 IU Twice/week | 50,000 IU Twice/week |
| Time Period | 1 month | 2 weeks | 6 weeks | 1 month | 9 weeks |
| Platelet Count | 72,000/mm³ | 301,000/mm³ | 89,000/mm³ | 244,000/mm³ | 176,000/mm³ |

| Treatment | F | G | H |
|---|---|---|---|
| Plaquenil ® | 200 mg Twice/day | 200 mg Twice/day | 200 mg Twice/day |
| Prednisone | 5 mg Once/day | 4 mg Once/day | 4 mg Once/day |
| Vitamin D | 50,000 IU Twice/week | 50,000 IU Twice/week | 50,000 IU Once/week |
| Time Period | 1 month | 6 weeks | 16 weeks |
| Platelet Count | 212,000/mm³ | 194,000/mm³ | 182,000/mm³ |

After 16 weeks, her platelet count remained high at 182,000/mm³; and prednisone was decreased to 2 mg/day.

The patient was put on a maintenance regime of Vitamin D at a dose of 50,000 IU/month, prednisone at a dose of 2 mg/day, and hydroxychloroquine at a dose of 400 mg/day, and 2.5 years after her initial presentation remained in remission with a platelet count of 169,000/mm³.

She continued to receive the maintenance regime for about another 18 months. The treatment regime was then adjusted to lower the dosage of both hydroxychloroquine (200 mg/day) and prednisone (2 mg/day), while maintaining the dosage of Vitamin D at 50,000 IU/month. She remains stable at the lower regime 4.5 years post-initial presentation.

Results.

The data in Table 2 illustrate that a combination of hydroxychloroquine and high doses of Vitamin D significantly increased the patient's platelet count from the extremely low initial count before treatment of 8,000 mm³ initial count to 212,000 mm³. Prior to beginning the Vitamin D and hydroxychloroquine treatment, the patient had been hospitalized in intensive care and received intravenous infusions of immunoglobulin, which was not successful in raising her platelet count. However, after only a one month treatment of Vitamin D and hydroxychloroquine, the platelet count increased from 8,000 mm³ to 72,000 mm³, and after an additional two weeks of treatment, the patient's platelet count had increased to well above normal levels (301,000 mm³).

As can be seen from the above treatment regimen, hydroxychloroquine at a dose of 200 mg a day and Vitamin D at a dose of 50,000 IU once a month, with very lose doses of prednisone (2 mg/day), was sufficient to maintain a stable platelet count of 169,000/mm³.

Example 3

Other patients with immune thrombocytopenia were treated with regimens similar to those described in Example 1 and Example 2 and similar results were observed (data not shown).

Example 4

Low levels of vitamin D have been implicated in a number of autoimmune disorders, such as rheumatoid arthritis, systemic lupus erythematosus, and Sjögren's syndrome. Patients with rheumatoid arthritis, systemic lupus erythematosus and Sjögren's syndrome were treated with a combination of weekly high doses of Vitamin D (50,000 IU) and daily doses of 400 mg of hydroxychloroquine. Restoration of the Vitamin D deficiency in these patients and treatment with hydroxychloroquine resulted in improved clinical status. Applicants have found that, in treating patients with autoimmune diseases other than ITP, increasing a patient's vitamin D level to the normal range of 40 ng/mL to 50 ng/mL can enhance the therapeutic response to standard treatment.

In the case of rheumatoid arthritis, it was also found that the patient's response to disease modifying anti-rheumatic drugs was enhanced after the Vitamin D deficiency was corrected with high dose Vitamin D replacement.

Because of the dramatic positive effect on the hematological complication (ITP) of systemic lupus erythematosus, it is expected that the Vitamin D and hydroxychloroquine treatment of the present disclosure will have a beneficial effect on other complications of SLE in patients who are Vitamin D deficient. Some of these complications include proteinuria, kidney disease, and/or skin disorders. It is felt that these patients have a similar immune dysfunction caused by a similar mechanism.

All body tissues and various organs have Vitamin D receptors. When a Vitamin D deficiency exists in the body, there is an interruption of the signaling from that receptor site. This in turn causes an immune dysfunction to occur and ultimately a disease state. Replenishing the Vitamin D in high doses can correct the deficiency and reverse the signaling disorder. This will prevent disease. Administering hydroxychloroquine in combination with Vitamin D enhances the effect of both drugs.

As illustrated in the data presented in the above Examples, applicants have found that administering high doses of vitamin D in combination with hydroxychloroquine to patients with immune thrombocytopenia results in a dramatic increase in platelet count, which is sustainable over many months, and even years. A possible explanation for this effect is provided in the discussion below.

There is evidence in the art that Vitamin D, or 1,25-dihydroxyvitamin D3 (1,25(OH)2D3), may be a potent immunomodulator. In 1991, researchers found that the production of interleukin IL-6 and IL-2 in cell cultures were reduced by 1,25(OH)2D3. See Muller K, Diamant M, Bendtzen K: "Inhibition of production and function of interleukin-6 by 1,25-dihydroxyvitamin D3," *Immunol Lett* 1991, 28(2):115-120. It was postulated that 1,25(OH)2D3 may inhibit the production and function of IL-6 and, therefore, regulate lymphocyte functions.

It has been documented that patients with immune thrombocytopenia have high rates of mononuclear cell proliferation as well as lymphocytes that secrete greater amounts of IL-2 compared to controls. See Andersson J: "Cytokines in idiopathic thrombocytopenic purpura (ITP)," *Acta Paediatr Suppl* 1998, 424:61-64. Researchers have also shown that in these patients, depleting CD8+ lymphocytes and complement did not reduce proliferation of mononuclear cells, which indicates that CD4+ T helper cells may be responsible for the response. In addition, the number of T regulatory cells in patients with ITP is markedly reduced. See Semple J W, Freedman J: "Increased antiplatelet T helper lymphocyte reactivity in patients with autoimmune thrombocytopenia," *Blood* 1991, 78(10):2619-2625. This suggests that stimulated CD4+ T helper cells mediate antibody production and maturation of B lymphocytes, and may contribute to the eventual autoantibody response targeting these patients' platelets.

Several studies have also shown that 1,25(OH)2D3 can inhibit the development of multiple sclerosis in the murine model. See Cantorna M T, Hayes C E, DeLuca H F: "1,25-Dihydroxyvitamin D3 reversibly blocks the progression of relapsing encephalomyelitis, a model of multiple sclerosis," *Proc Natl Acad Sci USA* 1996, 93(15):7861-7864; see also, Pedersen L B, Nashold F E, Spach K M, Hayes C E: "1,25-dihydroxyvitamin D3 reverses experimental autoimmune encephalomyelitis by inhibiting chemokine synthesis and monocyte trafficking," *J Neurosci Res* 2007, 85(11):2480-2490. Researchers suggest that CD4+ T cells may be the target of 1,25(OH)2D3 immunosuppression and studies have found that 1,25(OH)2D3 can inhibit T-cell proliferation and activation.

Other studies have shown that vitamin D stimulates transforming growth factor (TGF β-1) and IL-4 production, which in turn may suppress inflammatory T-cell activity. See Cantorna M T, Woodward W D, Hayes C E, DeLuca H F: "1,25-dihydroxyvitamin D3 is a positive regulator for the two anti-encephalitogenic cytokines TGF-beta 1 and IL-4," *J Immunol* 1998, 160(11):5314-5319; see also, Shevach E M: "Regulatory/suppressor T cells in health and disease," *Arthritis Rheum* 2004, 50(9):2721-2724. TGFβ-1 may help direct T-cell differentiation and promote the production of T regulatory cells via the Foxp3 transcription regulatory pathway resulting in the observed immunosuppression. See Pyzik M, Piccirillo C A: "The TGF-beta1/Foxp3 regulatory axis in immune self-tolerance: implications for health and disease," *Inflamm Allergy Drug Targets* 2006, 5(3):167-177. In fact, studies have shown that TGFβ-1 is able to promote T-cell differentiation from non-suppressor CD4+ T cells simply through Foxp3 induction. See Tran D Q, Ramsey H, Shevach E M: "Induction of FOXP3 expression in naive human CD4+ FOXP3 T cells by T-cell receptor stimulation is transforming growth factor-beta dependent but does not confer a regulatory phenotype," *Blood* 2007, 110(8):2983-2990. These T regulatory cells help suppress the immune response and thus maintain immune system homeostasis and tolerance to self-antigens.

Although the number of T-regulatory cells in ITP patients is significantly reduced, recent research has also shown that it is possible to generate T regulatory cells in vitro by pharmacologically manipulating the dendritic cells with glucocorticoid and 1,25(OH)2D3. See Unger W W, Laban S, Kleijwegt F S, van der Slik A R, Roep B O: "Induction of Treg by monocyte-derived DC modulated by vitamin D3 or dexamethasone: differential role for PD-L1," *Eur J Immunol* 2009, 39(11):3147-3159. Drug-induced effects on dendritic cells included induction of IL-10-secreting regulatory T cells, attenuation of IL-2 and interferon gamma secretion, prevention of T-cell IL-4 secretion, and suppression of antigen-specific primary T-cell proliferation. Overall, 1,25(OH)2D3 seems to have two important immunomodulatory functions: down-regulation of over proliferative CD4+ cells and concurrent up-regulation of T regulatory cells. Together, these effects may have the potential to reduce the autoantibody response and may potentially explain the restoration of platelet levels upon treatment of high-dose vitamin D in patients who have autoimmune thrombocytopenia.

In the above examples, an association between vitamin D deficiency and immune thrombocytopenia in two patients is described. Both patients had SLE and/or Sjögren's overlap with positive serology and profound life-threatening thrombocytopenia, all of which were unaffected by conventional therapies. High-dose replacement of Vitamin D plus the addition of Plaquenil® (hydroxychloroquine) and modest doses of steroids resulted in normalization of both patients' platelet counts. After discontinuation of supplemental Vitamin D in one patient (Example 1), the 25-OH Vitamin D normalized, but the platelet count subsequently plummeted. Resuming vitamin D supplementation restored the platelet count to the previous normal range. It is noteworthy that neither patient experienced any untoward side effect from high-dose Vitamin D, suggesting it is a safe alternative treatment to a life-threatening condition.

The results in Table 1 indicate that Vitamin D works synergistically with hydroxychloroquine through unknown mechanisms. It is clear from the results in Table 1 that hydroxychloroquine without Vitamin D resulted in a dramatic decrease in the patient's platelet count. Applicants have also found the combined regimen of hydroxychloroquine and Vitamin D works better than Vitamin D alone. It is expected that the combined treatment may also down-regulate the proliferation of CD4+ cells and up-regulate T regulatory cells. These combined effects may potentially reduce the autoantibody response.

The successful treatment of ITP can be variable, and the toxicity of many of the current treatments is considerable. The discovery and development of efficacious and non-toxic treatment for ITP is therefore imperative. Plaquenil® (hydroxychloroquine) has been used clinically for over 50 years and has an exceptional safety record. It is probably the safest among the disease-modifying agents that rheumatologists prescribe in the treatment of autoimmune diseases. Retinopathy is extremely rare, and the few reported cases were in patients taking the drug for more than 5 years. Baseline and annual eye exams are recommended. Other less common side effects include rash, tinnitus and muscle aches. It should not be prescribed to patients with glucose-6-phosphate dehydrogenase deficiency.

The Example 1 patient was treated with prednisone in addition to Vitamin D when platelet counts dropped subsequent to temporary Vitamin D discontinuation. Although it is possible prednisone was responsible for the platelet count recovery at 3 months post-clinic admission, this is unlikely for two reasons. First of all, the platelet count significantly decreased within one month of discontinuation of Vitamin D. The dosage of prednisone remained unchanged during this period. Secondly, the patient's platelet counts remained stable for 3 months without any prednisone treatment.

Applicants have found that the therapeutic dose of Vitamin D varies between 50,000 and 100,000 IU/week depending on the magnitude of the platelet count deficiency, and combined with a dose of hydroxychloroquine of 200 mg twice a day, is effective in treating patients with immune thrombocytopenia and other immune diseases.

The treatment protocol of the present disclosure, a combination of Vitamin D and hydroxychloroquine, is extremely cost effective (less than $100 per month). These costs are in sharp contrast to the high costs of alternative treatments of intravenous infusions and biologics, which can cost more than $10,000 per infusion, in addition to the costs of hospitalization. The present disclosure provides a treatment regimen that is safe and effective. Currently the existing treatments commonly used have many deleterious side effects. Some chemotherapeutic agents used for the treatment of ITP cause secondary cancer. Additionally, the treatment protocol of the present disclosure is very inexpensive, thus providing benefits to the patient, society in general and the government in reduction of health care costs.

While the present invention has been illustrated and described, it will be appreciated that various changes can be made therein without departing from the spirit and scope of the invention.

The embodiments of the invention in which an exclusive property or privilege is claimed are defined as follows:

1. A pharmaceutical composition for the treatment of immune thrombocytopenia purpura, wherein the composition consists of Vitamin D in a concentration of from about 7,500 IU to about 15,000 IU per unit dosage form, hydroxychloroquine in a concentration of from about 200 mg to about 400 mg per unit dosage form, and pharmaceutically acceptable excipients.

2. The pharmaceutical composition of claim 1, wherein the hydroxychloroquine is present in a concentration of about 200 mg per unit dosage form.

3. The pharmaceutical composition of claim 1, wherein the hydroxychloroquine is present in a concentration of about 400 mg per unit dosage form.

4. The pharmaceutical composition of claim 1, wherein the Vitamin D is present in a concentration of about 7500 IU per unit dosage form and the hydroxychloroquine is present in a concentration of about 200 mg per unit dosage form.

5. The pharmaceutical composition of claim 1, wherein the Vitamin D is present in a concentration of about 15,000 IU per unit dosage form and the hydroxychloroquine is present in a concentration of about 400 mg per unit dosage form.

* * * * *